United States Patent [19]

Cabre et al.

[11] Patent Number: 6,103,897
[45] Date of Patent: Aug. 15, 2000

[54] PRODUCTION OF A CRYSTALLINE SALT OF AMOXICILLIN

[75] Inventors: Joan Cabre; Jose Diago; Asuncion Esteve, all of Barcelona, Spain; Johannes Ludescher, Breitenbach, Austria

[73] Assignee: Biochemie Gesellschaft m.b.H., Kundl, Austria

[21] Appl. No.: 09/066,476

[22] PCT Filed: Oct. 28, 1996

[86] PCT No.: PCT/EP96/04682

§ 371 Date: Aug. 3, 1998

§ 102(e) Date: Aug. 3, 1998

[87] PCT Pub. No.: WO97/15579

PCT Pub. Date: May 1, 1997

[30] Foreign Application Priority Data

Oct. 26, 1995 [GB] United Kingdom .................... 9521921
May 28, 1996 [GB] United Kingdom .................... 9611088

[51] Int. Cl.$^7$ .................................................. C07D 499/16
[52] U.S. Cl. ............................................. 540/323; 540/335
[58] Field of Search ...................... 540/323, 335

[56] References Cited

U.S. PATENT DOCUMENTS

| 3,932,386 | 1/1976 | Nescio ................................. 260/239.1 |
| 4,014,868 | 3/1977 | Berry ........................................ 540/323 |
| 4,029,804 | 6/1977 | Clark et al. .............................. 424/271 |
| 4,737,585 | 4/1988 | Perez-Aranda Ortega et al. ... 540/321 |
| 5,559,241 | 9/1996 | Corsi et al. .............................. 548/178 |

FOREIGN PATENT DOCUMENTS

| 0 131 147A | 1/1985 | European Pat. Off. . |
| 0 176 716A | 4/1986 | European Pat. Off. . |
| 0 220 925A | 5/1987 | European Pat. Off. . |
| 0 596 262A | 5/1994 | European Pat. Off. . |
| 2 233 051A | 1/1975 | France . |
| 2 287 223A | 5/1976 | France . |
| 1286199 | 4/1971 | United Kingdom . |

OTHER PUBLICATIONS

Sykulski Chemical Abstracts, vol. 104, No. 16, Apr. 21, 1986 Abstract No. 135958.

*Primary Examiner*—Mark L. Berch
*Attorney, Agent, or Firm*—Lydia T. McNally; George R. Dohmann

[57] ABSTRACT

A process for the production of a crystalline salt of amoxicillin utilizing ethanol as a solvent, and crystallizing the salt of amoxicillin in the presence of a salifying compound.

8 Claims, No Drawings

PRODUCTION OF A CRYSTALLINE SALT OF AMOXICILLIN

This application is a 371 of PCT/EP96/04682, filed Oct. 28, 1996.

This invention relates to a process for the production of the salt, e.g. the sodium salt, of the penicillin antibiotic amoxicillin. Sodium amoxicillin is a well known penicillin widely used for parenteral preparations.

When sodium amoxicillin is made by spray-drying or freeze-drying of an aqueous solution the content of degradation products may be extremely high and therefore the assay of the product low. Normally commercially available sodium amoxicillin obtained by spray-drying may be very unstable and may have a high content of by-products.

Crystalline sodium amoxicillin is a preferred form of sodium amoxicillin. A process for its production in a mixture of solvents via a solvate of sodium amoxicillin and removing the solvating solvent therefrom is disclosed, for example, in EP-B-0 131 147. The mixture of solvents required results in the use of large amount of solvents and in a complicated and expensive recovery system requiring generally the incineration of several kilograms of solvents per kilogram of sodium amoxicillin. For example, according to example 22 of EP-B-0 131 147, wherein the highest yields are disclosed, per kilogram of sodium amoxicillin about 80 l of a solvent mixture (methanol, methyl acetate, methylene chloride) has to be used. Efficient solvent recovery is difficult since methanol forms azeotropes with methylene chloride and methyl acetate. Probably for this reason practically all commercially available sodium amoxicillin has been obtained by spray-drying despite the previously mentioned quality problems.

EP-B-0 596 262 describes a further sodium amoxicillin production process. However, the solvent mixture used is even more complex than according to EP-B-0 131 147 in that, apart from methanol and methyl acetate, still a further $C_{2-5}$ alcohol is used.

Surprisingly we have now found a new process for the production of a salt, e.g. sodium, of amoxicillin which overcomes the deficiencies of prior art processes, i.e. an industrially applicable, simple process, using only low volumes of a simple solvent system, even essentially one single solvent, wherein the salt, e.g. sodium, of amoxicillin crystallizes giving surprisingly excellent yields and quality of the product.

In one aspect the present invention provides therefore a process for the production of a crystalline salt of amoxicillin in ethanol as solvent, e.g. crystallising said salt from an essentially ethanolic solution. The crystalline salt may be produced, e.g. as disclosed with reference to step (ii) below.

In a further aspect the present invention provides a process for the production of a crystalline salt of amoxicillin which is characterized by the steps
  (i) dissolving amoxicillin in ethanol,
  (ii) crystallizing the salt of amoxicillin in the presence of a salifying compound.

Step (i) may be carried out as follows:

Amoxicillin, e.g. trihydrate or partially anhydrified, preferably trihydrate, may be dissolved, e.g. in ethanol, e.g. in the presence of a solubilizing agent, for example a base, including a suitable amine. As used herein the term amine includes a mixture of amines. Amoxicillin may react with the base to give a salt of amoxicillin; for example in case of an amine, to give an amine salt, or in case of a mixture of amines to give a mixture of amine salts of amoxicillin. A further solvent, for example methyl acetate, may be present.

In a further aspect the present invention provides a process for the production of a crystalline salt of amoxicillin which is characterized by the steps
  (i) producing an amine salt of amoxicillin in ethanol,
  (ii) crystallizing the salt of amoxicillin in the presence of a salifying compound.

An amine salt of amoxicillin may be produced by contacting amoxicillin with an amine or a mixture of amines. Preferred amines include $C_{1-4}$ trialkyl or dialkyl amines. Preferably the alkyl groups in each of the di- or trialkylamines are identical. Especially preferred are triethylamine, diethylamine and diisopropylamine. A mixture of amines is preferred. Preferably the amine mixture contains two different amines, in, for example, a ratio of about 1.5:1 to 5:1, e.g. of about 2:1 to 3:1. It is especially preferred to use a mixture of trialkylamines and dialkylamines, for example of triethylamine and diisopropylamine. e.g. in a ratio as defined above. Preferably the alkyl groups of the trialkylamine are different from the alkyl groups of the dialkylamine. An amine may be used in an appropriate amount in respect to amoxicillin, for example in an amount as usually usable. At least equivalent amounts, for example an excess of the amine may be used, e.g. per mol amoxicillin trihydrate about 1.0 to 2.5, for example 1.1 to 2.5 mol of the amine may be appropriate.

In a further aspect the present invention provides a process for the production of a crystalline salt of amoxicillin which is characterized by the steps
  (i) producing an amine salt of amoxicillin in ethanol,
  (ii) crystallizing the salt of amoxicillin in the presence of a salifying compound,
wherein in step (i) amoxicillin is reacted with a mixture of amines.

Step (ii) comprises precipitation of the salt, e.g. sodium, of amoxicillin from the reaction mixture. Step (ii) may be carried out in the presence of a salifying compound, for example by treating dissolved amoxicillin, e.g. an amine salt of amoxicillin with a salifying compound.

In another aspect the present invention provides a process for the production of a crystalline salt of amoxicillin wherein a salt of amoxicillin is crystallized from a mixture of an amine salt of amoxicillin with a salifying compound in ethanolic solution, e.g. an amine salt of amoxicillin may be treated with a salifying compound and the product may be crystallized from essentially ethanolic solution.

As used herein and if not otherwise stated the term a salt of amoxicillin includes a salt of amoxicillin with different cations, for example alkali or earth alkali cations, such as sodium, potassium or magnesium, preferably sodium. Such salts may be obtained using the appropriate salifying compound.

The salifying compound may be reacted with the amine salt of step (i), for example, in solution, for example in ethanolic solution. A salifying compound includes preferably a pharmaceutically acceptable salifying compound, e.g., the salt of an organic compound, for example, an alcoholate, e.g. $C_{1-8}$, such as methoxide, ethoxide; and a salt of an organic acid, e.g. $C_{1-12}$, such as 2-ethylhexanoate, pivalate or diethylacetate; preferably an alcoholate, e.g. $C_{1-4}$ or a carboxylate; more preferably a carboxylate, e.g. $C_{1-8}$, such as 2-ethylhexanoate. A salifying compound is preferably a sodium salt.

In another aspect the present invention provides a process for the production of a crystalline salt of amoxicillin in ethanol, wherein the sodium salt of amoxicillin is produced.

An ethanolic solution of step (ii) may contain beside amoxicillin, ethanol and the salifying compound, for example amounts of the amine originating from the amine salt of amoxicillin in step (i) and water, originating for example from the trihydrate of amoxicillin used for formation of the amine salt of amoxicillin in step (i) and/or from addition of an aqueous inorganic salt; or if used, which is however less preferable, another solvent, such as for example methyl acetate.

The salt of amoxicillin may crystallise upon contact of the amoxicillin, dissolved for example in form of an amine salt thereof, with the salifying agent. Dissolved amoxicillin may be contacted with the salifying agent for example under stirring, for example in the presence of seed crystals. Seed crystals are preferably such, which are obtainable according to the process of the present invention, for example according to the examples. The contact temperature of the dissolved amoxicillin and the salifying agent is not critical and may be, for example less than 0° C. to about room temperature, for example 5° C. and about 25°, such as 10° C. to 14° C. The crystall suspension may be stirred and cooled to achieve complete crystallization.

The reaction mixture containing a crystalline salt, e.g. sodium, of amoxicillin may be worked up in usual manner, for example by filtrating off the crystals and drying.

The amount of ethanol used for the production of a crystalline salt of amoxicillin from. for example amoxicillin trihydrate, is not critical in respect to crystallisation of the salt of amoxicillin, but for obtaining high yields ethanol should not be used in too large amounts. For example, amounts of about 5 ml to about 25 ml and more, preferably about 8 ml to 20 ml, for example about 8 ml to 15ml, such as about 10 ml to 12 ml ethanol per gram of amoxicillin trihydrate may be used.

The salt of amoxicillin may be mixed during some reaction step or after the isolation with inorganic salts, e.g. sodium salts, for example carbonates, such as sodium carbonate, or alcoholates, such as ethoxide, in order to achieve special solubility properties. The inorganic salt may be added for example during crystallisation step (ii). The salt may be added for example in aqueous or ethanolic solution and may crystallize in mixture with the salt of amoxicillin.

A preferred embodiment of the invention provides a process for the production of sodium amoxicillin which comprises the steps of i) dissolving amoxicillin trihydrate in ethanol in the presence of an amine, and ii) further reacting the resultant solution with a sodium salt of an organic compound in ethanol.

Steps (i) and (ii) may be performed in one single solvent, i.e. ethanol. Per gram of amoxicillin trihydrate about 8 ml to 15 ml, for example 10 ml to 12 ml of ethanol may be used in steps (i) and (ii). Dissolution of amoxicillin may be effected by forming an amine salt of amoxicillin, for example by contacting an amine, for example triethylamine or diisopropylamine, preferably a mixture of amines, such as a mixture of a trialkylamine and a dialkylamine, for example a mixture of triethylamine and diisopropylamine, for example in a ratio of about 2:1 to 3:1, with amoxicillin trihydrate, preferably in ethanolic solution, for example at temperatures below 0° C. and 15° C., such as 0° C. to 5° C. The mixture may be stirred at temperatures of about 8° C. to room temperature, for example about 0° to 20° C., such as 10° C. to 15° C., in order to obtain complete solution. A salifying compound, preferably a sodium carboxylate, e.g. $C_{1-8}$, such as 2-ethylhexanoate, preferably in ethanolic solution, may be added to the solution of amoxicillin, for example at a temperature of about 5° C. to about 25° C., such as 10° C. to 14° C. Seed crystals of crystalline sodium amoxicillin may be present. Crystalline sodium amoxicillin may crystallise upon contact of the salifying agent with dissolved amoxicillin, for example upon contact with a dissolved amine salt of amoxicillin. The mixture may be stirred for some time, for example at addition temperatures and cooled, for example to about less than 0° C. to about 10° C., for example about 0° C. to 5° C. in order to obtain complete crystallisation. The crystalline sodium salt of amoxicillin may be isolated, for example by filtration, and dried. The isolated product is easy to dry—even good results are obtained at room temperature.

In another aspect the present invention provides the use of ethanol as solvent in the crystallization of a salt, e.g. the sodium salt, of amoxicillin.

The use of ethanol has surprising and important advantages:

It dissolves organic salts of amoxicillin. Therefore no additional solvents are required.

It does not dissolve remarkable quantities of sodium amoxicillin. Therefore no additional solvents are required.

No significant amounts of ethanol are retained in the final product as residual solvent.

Ethanol is a solvent with low toxicity.

Recovery of ethanol after the process is easy and conventional.

The higher stability of ethanolic amoxicillin solutions compared to methanolic.

As a consequence the present invention provides a process for producing a salt, e.g. the sodium salt of amoxicillin having a number of significant and economical advantages. The final product of excellent quality may be isolated from a reaction mixture containing essentially ethanol as organic solvent, if desired, under very concentrated conditions and with high yields and consequently high productivity. There is no need for any further component, other than the salifying compound, and when step (i) is present the solubilizing compound and ethanol, i.e. no need for methanol or an aprotic solvent, such as, for example methylene chloride.

High isolation yields of crystalline sodium amoxicillin may be achieved having, for example the following main characterics:

Assay, e.g. by HPLC on anhydrous basis: hi-her than 96% (for example about 96.5 to about 100%, e.g. 99.5%)

Degradation products (for example the dimer of amoxicillin, or p-hydroxy-phenylglycyl amoxicillin): lower than 2.5%, for example lower than 1.5% (for example less than about 0.7% to 1.2%)

Residual solvents (ethanol): less than 0.5%, e.g. less than 0.32% to less than 0.5%)

Residue from salifying compound (residue from sodium carboxylate); less than 0.21%, for example 0.2% to 0.39%, for example 0.38%

Water (for example from amoxycillin trihydrate or from addition of an aqueous inorganic salt): less than 0.8%, for example less than 0.52%.

A crystalline salt of amoxicillin, e.g. sodium, containing ethanol, for example less than 0.32% such as 0.31% to less than 5%, such as less than 4%, 3%, 2%, 1% or 0.5%, e.g. 0.49% ethanol is new and also forms part of the invention.

In another aspect the present invention provides a crystalline salt of amoxicillin, e.g. sodium, containing ethanol, for example less than 5%, such as less than 0.8%.

Furthermore the process of the invention permits one to work with low volumes of ethanol. Quantities in the range of 7 to 20 l of ethanol per kilogram of sodium amoxicillin have been used with good results.

The following non-limitative examples illustrate the invention. All temperatures are in degrees Centigrade and are uncorrected.

In the examples the following abbreviations are used:
AMOT: Amoxicillin trihydrate
2-EHNa: 2-Ethylhexanoate sodium
TEA: Triethylamine
DIPA: Diisopropylamine
SOR: Specific optical rotation
DP: Degradation Products Results of the assay (HPLC based on the salt) and the SOR are given on an anhydrous basis. Where DP not given this is less than about 2.5%. HPLC for amoxicillin is as described in US Pharmacopeia. Contents of DP, EtOH, residue of salifying compound determined by HPLC. Water content determined by K.F. method. Low vaccuum is about 0.5 to 0.8 mm.

Preparation of crystalline sodium amoxicillin

EXAMPLE 1 i) 20 g of AMOT are added to a solution of 13.6 ml of TEA in 20 ml of ethanol keeping the temperature at 0–5°. The system is washed with 10 ml of ethanol. The resultant mixture is stirred for some minutes at 10–15° in order to get complete solution. 60 ml of ethanol are added and the solution is filtered and washed with 40 ml of ethanol (preparation A).

ii) 13.86 g of sodium 2-EHNa are dissolved in 45 ml of ethanol (preparation B). Preparation B is filtered into a container and added to preparation A within about 15 minutes keeping the temperature at 10–12°. The container of preparation B is washed with 25 ml of ethanol. 0.4 g of crystalline sodium amoxicillin (inoculum) are added. Stirring is continued at 10–12° for 60 minutes and the reaction mixture is cooled to 0–5° for 90 minutes. Crystalline sodium amoxicillin is obtained, filtrated off, washed with 40 ml of ethanol and dried in low vacuum. Yield: 15.55 g (82.0%). Assay (HPLC): 98.9%. SOR: 287.8°. Water content: 0.51%. DP content: 0.65%. Ethanol content: 0.31%. Content of 2-ethylhexanoic acid: 0.29%.

EXAMPLE 2 i) 20 g of AMOT are added to a solution of 13.6 ml of TEA in 20 ml of ethanol keeping the temperature at 0–5°. The system is washed with 10 ml of ethanol. The resultant mixture is stirred for some minutes at 10–150 in order to achieve complete solution. 50 ml of ethanol are added (preparation A).

ii) 13.86 g of 2-EHNa are dissolved in 95 ml of ethanol. The solution is filtered and the filter is washed with 15 ml of ethanol. 0.4 g of crystalline sodium amoxicillin (inoculum) are added (preparation B). Preparation A is filtered and added to preparation B within about 15 minutes keeping the temperature at 10–12°. The container of preparation A is washed with 10 ml of ethanol. Stirring is continued at 10–12° for about 60 minutes. The reaction mixture is cooled to 0–5° for 90 minutes. Crystalline sodium amoxicillin is obtained, filtrated off, washed with 40 ml ethanol and dried in low vacuum. Yield: 15.74 g (83.0%). Assay (HPLC): 99.5%. SOR: 284.5°. Content of 2-ethylhexanoic acid: 0.38%. Water content: 0.5%.

EXAMPLE 3 i) 20 g of AMOT are added to a solution of 13.6 ml of TEA in 20 ml of ethanol keeping the temperature at 0–5°. The system is washed with 10 ml of ethanol. The resultant mixture is stirred for some minutes at 10–15° C. in order to achieve complete solution. 97 ml of ethanol are added. The solution is filtered and washed with 10 ml of ethanol (preparation A).

ii) 13.86 g of 2-EHNa are dissolved in 35 ml of ethanol (preparation B). Preparation B is filtered and at the same time added to preparation A within about 5 minutes keeping the temperature at 10–12°. The filter is washed with 15 ml of ethanol. 0.4 g of crystalline sodium amoxicillin (inoculum) are added. Stirring is continued for 30 minutes at 10–12°. A white slurry is obtained. 8.0 g of a filtered solution of crystalline sodium ethoxide 21% (w/w) in ethanol are added within 5 minutes. The mixture is stirred for 30 minutes keeping the temperature at 10–12°. The mixture is stirred for 2 hours at 0/5° C. and worked up in analogous manner as described in example 1. Yield of crystalline sodium amoxicillin: 16.29 g (86.0%). Assay (HPLC): 96.9. SOR: 284.5°. Ethanol content: 0.47%. Content of 2-ethylhexanoic acid: 0.33%.

EXAMPLE 4

Example 2 is repeated with the following changes:

a) 7.37 ml of DIPA are used instead of 13.6 ml of TEA in step i). Yield of crystalline sodium amoxicillin: 15.56 g (82.0%). Assay (HPLC): 99.4%. SOR: 285.4°. DP content: 1.2%.

b) 9.98 ml of TEA are used instead of 13.6 ml of TEA in step i). Yield of crystalline sodium amoxicillin: 15.25 g (80.4%). Assay (HPLC): 99.0%. SOR: 283.6°. DP content: 1.2%. Ethanol content: 0.49%.

c) 10.37 g of sodium pivalate are used instead of 13.86 g of 2-EHNa in step ii). Yield of crystalline sodium amoxicillin: 14.45 g (76.0%). SOR =282.8°. Content of pivalic acid: 0.2%.

d) 19.79 g of 2-EHNa are used instead of 13.86 g of 2-EHNa in step ii). Yield of crystalline sodium amoxicillin: 15.89 g (83.8%). Assay (HPLC): 98.8%. SOR= 286.5°. DP content: 1.1%. Content of 2-ethylhexanoic acid: 0.36%. Ethanol content: 0.44%

EXAMPLE 5

Example 3 is repeated with the following changes:

a) 7.37 ml of DIPA are used instead of 13.6 ml of TEA in step i). Yield of crystalline sodium amoxicillin: 16.01 g (84.5%). Assay (HPLC): 96.5%. SOR: 279.6°. Content of 2-ethyihexanoic acid: 0.33%. Ethanol content: 0.52%.

b) 7.37 ml of DIPA are used instead of 13.6 ml of TEA in step i) and 10.37 g of sodium pivalate are used instead of 13.86 g of 2-EHNa in step ii). Yield of crystalline sodium amoxicillin: 15.21 g (80.1%). Assay (HPLC): 96.5%. SOR: 283.6°. Content of pivalic acid: 0.21%.

EXAMPLE 6 i) 20 g of AMOT are added to a solution of 8.51 ml of TEA and 3.52 ml of DIPA in 45 ml of ethanol keeping the temperature at 0–5°. The system is washed with a mixture of 10 ml of ethanol and 1.2 ml of TEA. The resultant mixture is stirred for about 15 minutes at 0 to 50° in order to achieve complete solution and filtered. The filter is washed with a mixture of 10 ml of ethanol and 0.4 ml of TEA (preparation A).

ii) 13.86 g of sodium 2-EHNa are dissolved in 25 ml of ethanol and the system is washed with 10 ml of ethanol and filtered. The filter is washed with 10 ml of ethanol (preparation B).

iii) To a suspension of 0.8 g crystalline sodium amoxicillin (inoculum) in 90 ml of ethanol are simultaneously added preparation A and preparation B within about 30 minutes keeping the temperature at ca. 12 to 14° under stirring. Stirring is continued at 12 to 14° for ca. 30 minutes. 1.35 g of a 22% aqueous sodium carbonate solution are added and the reaction mixture is stirred for ca. 30 minutes at ca. 12 to 14° and for ca. 90 minutes at ca. 5° and cooled to 0–5° for 90 minutes. Crystalline sodium amoxicillin is obtained, filtrated off, washed with 40 ml of ethanol and dried in low vacuum. Yield: 16.3 g (84.0%). Assay (HPLC): 97.1%. SOR: 281.7°. Water content: 0.76%. DP content: 0.8%.

We claim:

1. A process for the production of a crystalline salt of amoxicillin with alkali or earth alkali cations, which is characterized by the steps of
    (i) dissolving amoxicillin in ethanol, and
    (ii) crystallizing the salt of amoxicillin in the presence of a salifying compound wherein the salifying compound is a salt of an alcoholate or a salt of an organic acid.

2. A crystalline salt of amoxicillin with alkali or earth alkali cations containing ethanol.

3. A process for the production of a crystalline salt of amoxicillin with alkali or earth alkali cations, which is characterized by the steps of
    (i) dissolving amoxicillin in ethanol in the presence of an amine, and
    (ii) crystallizing the product in the presence of a salifying compound, wherein the salifying compound is a salt of an alcoholate or a salt of an organic acid.

4. A process according to claim 1, wherein in step (i) amoxicillin is reacted with a mixture of amines.

5. A process for the production of a crystalline salt of amoxicillin with alkali or earth alkali cations, wherein the salt of amoxicillin is crystallized from a mixture of an amine salt of amoxicillin with a salifying compound in ethanolic solution, wherein the salifying compound is a salt of an alcoholate or a salt of an organic acid.

6. A process according to claim 1, wherein the sodium salt of amoxicillin is produced.

7. A process for the production of sodium amoxicillin which comprises the steps of
    (i) dissolving amoxicillin trihydrate in ethanol in the presence of an amine, and
    (ii) further reacting the resultant solution with a sodium salt of an alcoholate in ethanol.

8. A process according to claim 7, wherein in step (i) a mixture of amines is used.

* * * * *